United States Patent
Jacobs et al.

(10) Patent No.: US 9,310,286 B2
(45) Date of Patent: Apr. 12, 2016

(54) PATIENT SAMPLE CLASSIFICATION BASED UPON LOW ANGLE LIGHT SCATTERING

(75) Inventors: Merrit N. Jacobs, Fairport, NY (US); Michael W. Sundberg, Pittsford, NY (US); Zhong Ding, Pittsford, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 677 days.

(21) Appl. No.: 12/779,358

(22) Filed: May 13, 2010

(65) Prior Publication Data

US 2010/0221757 A1    Sep. 2, 2010

Related U.S. Application Data (62) Division of application No. 10/968,524, filed on Oct. 19, 2004, now abandoned.

(60) Provisional application No. 60/513,753, filed on Oct. 23, 2003.

(51) Int. Cl.
| | | |
|---|---|---|
| *G01N 15/04* | (2006.01) | |
| *G01N 33/80* | (2006.01) | |
| *G01N 33/49* | (2006.01) | |
| *G01N 15/05* | (2006.01) | |
| *G01N 15/02* | (2006.01) | |

(52) U.S. Cl.
CPC .............. *G01N 15/042* (2013.01); *G01N 15/05* (2013.01); *G01N 33/4905* (2013.01); *G01N 15/0211* (2013.01); *G01N 33/80* (2013.01)

(58) Field of Classification Search
None
See application file for complete search history.

(56) References Cited

U.S. PATENT DOCUMENTS

| | | | |
|---|---|---|---|
| 3,809,478 A | 5/1974 | Talbot | 356/71 |
| 4,252,538 A | 2/1981 | Barr | 435/7.25 |
| 4,452,902 A | 6/1984 | Suovaniemi et al. | 436/517 |
| 4,720,465 A | 1/1988 | Jensen et al. | 436/523 |
| 4,762,413 A | 8/1988 | Namba et al. | 356/339 |
| 4,933,291 A | 6/1990 | Daiss et al. | |
| 5,100,805 A | 3/1992 | Ziege et al. | 436/517 |
| 5,369,037 A | 11/1994 | Hansen | |
| 5,512,432 A | 4/1996 | Lapierre et al. | |
| 5,552,064 A | 9/1996 | Chachowski et al. | 210/787 |
| 5,594,808 A | 1/1997 | Shen et al. | |
| 5,768,407 A | 6/1998 | Shen et al. | |
| 5,905,808 A | 5/1999 | Shen et al. | |
| 5,939,326 A * | 8/1999 | Chupp et al. | 436/43 |
| 6,153,148 A | 11/2000 | Thomas | 422/72 |
| 6,203,706 B1 | 3/2001 | Schwind et al. | |
| 2002/0076826 A1 | 6/2002 | Jacobs et al. | |
| 2002/0081747 A1 | 6/2002 | Jacobs et al. | 436/174 |
| 2002/0149763 A1 | 10/2002 | Tsukada | |
| 2002/0196435 A1 | 12/2002 | Cohen et al. | 356/246 |
| 2007/0206203 A1 | 9/2007 | Trainer | 356/521 |

* cited by examiner

*Primary Examiner* — Neil N Turk
(74) *Attorney, Agent, or Firm* — Barclay Damon, LLP (57) ABSTRACT

An apparatus for classifying a liquid patient sample includes at least one sample container having a quantity of a sample that is aggressively acted upon so as to create a flow field. A measurement mechanism includes at least one low angle light emitter aligned with a measurement window of the at least one sample container and a detector oppositely disposed relative to the measurement window. Measurement of the scattered light detects particle characteristics of a moving flow field from the sample to determine, for example, the amount of agglutination of the sample so as to perform blood typing or other classifications without spatial separation.

5 Claims, 6 Drawing Sheets

PATIENT SAMPLE CLASSIFICATION BASED UPON LOW ANGLE LIGHT SCATTERING

CROSS REFERENCE TO RELATED APPLICATION

This application is a divisional application of U.S. Ser. No. 10/968,524, filed Oct. 19, 2004 now abandoned, which is a non-provisional patent based upon U.S. Ser. No. 60/513,753, filed Oct. 23, 2003, each filed pursuant to relevant sections of 35 USC §119 and 35 USC §120, the entire contents of each application being incorporated herein by reference.

FIELD OF THE INVENTION

The invention is directed to the field of clinical chemistry and more particularly to apparatus and a related method for blood typing patient samples.

BACKGROUND OF THE INVENTION

Currently known column blood-typing systems, including, for example, the AutoVue systems manufactured by Ortho Clinical Diagnostics Inc., of Raritan, N.J., among others, were originally optimized for manual testing. As a consequence, a number of characteristics of the systems, while supporting the manual determination of a positive reaction, do not support facile automation.

First, agglutination strength is determined in a manner that is optimized for a subjective visual read. This determination is based upon a perceived distribution of red color from red blood cells, RBCs, in an elongated column, with an agglutinated sample being characterized by red color that is distributed above the bottom of the column, with a non-agglutinated sample having red color localized at the bottom thereof.

Automated reading of the distribution of red color is complex and requires a vision system that is coupled with relatively sophisticated software algorithms in order to appropriately classify the wide range of color distribution patterns that can be encountered. Such a technique is described, for example, in U.S. Pat. Nos. 5,594,808 and 5,768,407.

In these systems, a centrifugation step of relatively long duration (e.g., approximately 15 or 20 minutes) is typically required in order to achieve a necessary spatial separation of the agglutinated from the unagglutinated cells, including both incubation and centrifugation times.

Analysis of agglutination patterns however, is often an urgent procedure, for example in the case of injury, and the elimination of time in the blood typing process is therefore highly significant and greatly desired in the field.

A technique that permits agglutination to be detected without centrifugation has been more recently described by Applicants' in U.S. Pat. No. 7,452,508 and U.S. Patent Publication No. US 2002/0081747, each of which is incorporated by reference in its entirety. This technique defines apparatus and a method for aspirating within a probe tip and is defined such that most of the liquid diameters of the tip to cause rotational mixing of the liquid. This method is useful in providing agglutination of blood, which can then in turn be used in blood typing. The classification and determination of agglutination strength, however, regardless of the technique used to cause separation, is the same as described above, e.g., thereby requiring spatial separation of the agglutinated/unagglutinated cells.

SUMMARY OF THE INVENTION

It is therefore a primary object of the present invention to alleviate or substantially minimize the above-noted deficiencies of the prior art.

It is another primary object of the present invention to provide a blood typing methodology that is more efficient in terms of time and accuracy than any previously known typing technique.

It is yet another primary object of the present invention to provide an agglutination reaction detection system and a related method that is not solely dependent upon spatial separation in order to be able to detect the amount of agglutination of a sample liquid.

Therefore and according to a preferred aspect of the present invention, there is described a method of classifying a patient sample, said method including the steps of:

providing a mixture of a blood sample and an agglutination reagent into the confines of a sample container;

moving the mixture within the sample container such that an agglutination reaction occurs and that the agglutinated cells are moved as a flow field past a measurement window of the sample container;

aiming a light source into the sample container and probing the flow field with the light beam; and detecting the number and size of particles in the light beam to determine the amount of agglutination of said sample.

According to one technique, the mixture is moved by means of a vertical (e.g., up and down) movement of the sample within a reaction vessel serving as the sample container in order to mix the sample and to move the agglutinated cells through at least one defined transition zone of the vessel, the transition zone having a smaller inside diameter than the adjacent portion through which the sample is moved under the force of gravity. In this manner, agglutinated material is separated from non-agglutinated material.

According to another technique, the sample container can be centrifuged using at least one fluid having a viscosity and specific gravity that effectively excludes the sample prior to centrifugation, but which allows the particles to enter when the centrifugal force is applied, while excluding small molecules and controlling the rate at which the material moves within the fluid under the centrifugal field.

According to the present technique, a cloud of cells are formed in the sample container. A low-angle particle measurement system comprising at least one light emitter and at least one light detector is used to detect the agglutination in the cloud of cells at specified times after initiating the reaction.

Preferably, the sample container is elongated in configuration and includes a flat planar wall defining the measurement window for permitting the light beam to be effectively scattered by the particles contained in the moving flow field. According to another preferred aspect of the invention, there is described an apparatus for classifying a patient sample, said apparatus including:

at least one sample container;

means for moving a quantity of sample fluid contained within said at least one sample container so as to create a moving flow field; and a measurement mechanism including a light emitter aligned with a measurement window of said at least one sample container and a light detector oppositely disposed relative to said measurement window for detecting scattered light from an emitted light beam, wherein said detector detects particle characteristics of said flow field in order to effectively classify said sample, Preferably, the light source emits a beam that scatters at low angles based upon the number and size of particles in a scanning measurement volume wherein the aligned detector receives the scattered light and through processing logic contained therein is able to detect the amount of agglutination based on the detected particle distribution, so as to perform blood typing or other detection analyses of a patient sample.

An advantage of the herein described measurement system and method is that blood typing and other detection analyses can be performed in a much more time effective manner than previously known techniques. Moreover, the newly described technique does not require the use of an inert bead matrix or other similar means as typically required, for example, in agglutination detection processes that require spatial separation of agglutinated and unagglutinated cells, such as those described, for example, in U.S. Pat. Nos. 5,512,432 and 6,203,706B1, among others that require spatial separation in order to effectuate a visual determination of agglutination strength.

It will be readily apparent that the above method can be used to detect other target antibodies or antigens, proteins, viruses, or bacteria in a similar manner by producing a cloud of particles in a reaction and determining the degree of agglutination using a low angle light scattering means and a suitable measurement system to determine the particle distribution from a scanned beam impinging upon the moving flow field.

An advantage provided by the apparatus and method of the present invention is that blood typing and other forms of classification by reaction can be performed in an extremely fast and efficient manner without requiring spatial separation.

Yet another advantage of the present invention is that the herein described system and method can be added to already existing equipment without significant modification thereto.

Yet another advantage of the present invention is that the above described method provides an effective qualitative determination of agglutination strength.

These and other objects, features and advantages will be apparent from the following Detailed Description which should be read in conjunction with the accompanying drawings.

DETAILED DESCRIPTION

The following description relates to certain preferred embodiments of the present invention, and to a particular methodology for blood typing by detection of agglutination strength by means of a low angle light scattering/detection system. As will be readily apparent from the discussion, the inventive concepts described herein can also be suitably applied to other reaction processes in addition to blood typing to detect antigens, antibodies, proteins, viruses, and the like wherein a reaction can create a moving flow field. In addition, such terms as "top", "bottom", "lateral", "above", "below" and the like are also used in order to provide a convenient frame of reference for use with the accompanying drawings. These terms, unless stated specifically otherwise, however, are not intended to be limiting of the present invention.

Figure 1:
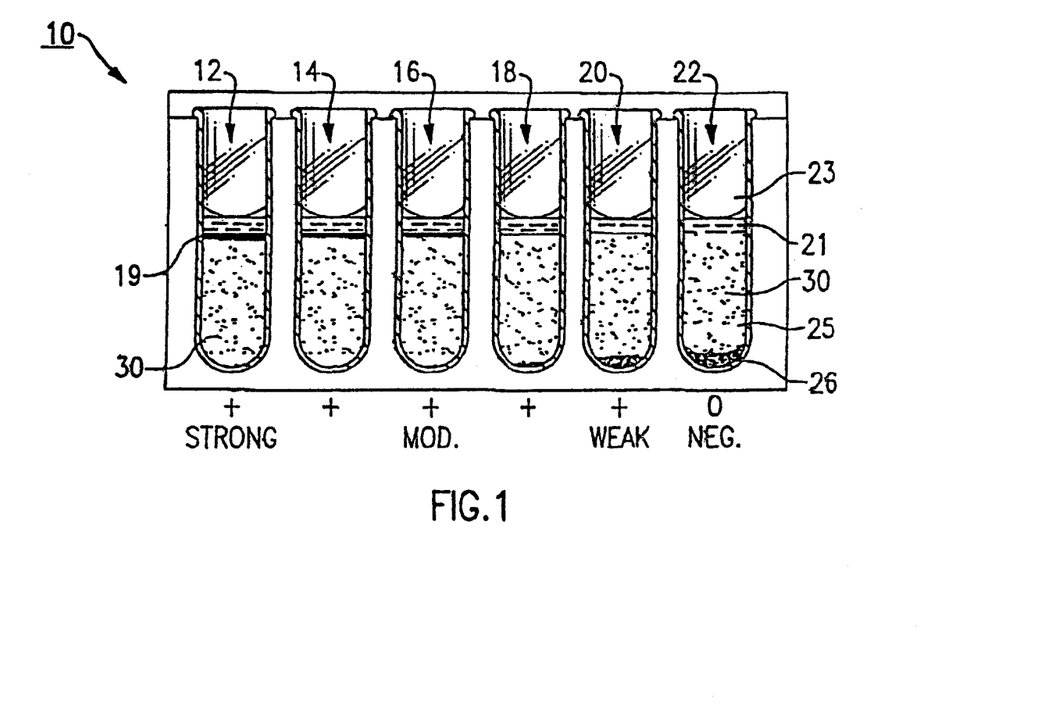
FIG. 1 is a cross-sectional view of a prior art test tube cartridge containing multiple samples showing the patterns occurring in positive, weakly positive, and negative agglutination reactions for column agglutination assays.

Referring to FIG. 1, the results of a prior art blood typing system are herein described briefly for purposes of background. In this system, as more completely described in U.S. Pat. No. 5,552,064 incorporated entirely by reference herein, a series of tubular sample containers 14, 16, 18, 20, 22 are disposed within a cartridge 10. Each of the tubular sample containers includes a suspended matrix 30 of substantially noncompressible inert microparticles that permit movement of nonagglutinated reactants, such as red blood cells, while constraining agglutinated reactants. The matrix 30 is typically suspended within a gel in a lower portion 25 of the container, the gel having a density that is slightly lower than of the red blood cells to promote movement therethrough. Typically and for ABO blood typing, a sample and agglutination reactant is first received within an upper portion 23 or chamber of each container in the form of serum and cells that are incubated prior to movement through the matrix 30 of suspended particles. The upper portion 23 is separated from the lower portion 25 by means of a separating orifice having a diameter permitting the passage of cells therethrough, the serum and cell reagent being applied so as to create an air pocket or bubble between the upper portion and the reminder of the container. A user then applies a sufficient force, typically centrifugation, to effect this movement wherein a band of agglutinated reactants is formed above the matrix 30 for visual or automated detection. The container may also have an initial reaction zone 21.

As noted, FIG. 1 illustrates a range of spatial separation patterns that are representative of positive, weekly positive, and negative agglutinations. Tubular sample container 12 demonstrates a strong positive reaction with a firm band 19 of agglutinates. Container 14 shows a positive reaction that is somewhat weaker than that shown in container 12, as the agglutinate band has broken apart into smaller agglutinates. Container 16 demonstrates a weaker positive reaction with a smaller quantity of agglutinates being distributed throughout the middle portion of the matrix, and even settling on the bottom, as in container 18. Container 20 depicts a very weak positive reaction, with most of the cells being collected on the bottom. Finally, tubular sample container 22 depicts a clear negative reaction, with a button of cells 26 located on the bottom of the container, and no agglutinates dispersed within the matrix 30.

The present invention relates to use of a technique of low-angle light scattering to provide a more accurate and repeatable determination of agglutination without requiring spatial separation. The basic theory of this technique follows:

Low-angle light scattering is generally based on the principle that the absorption coefficient and the volume scattering function (VSF) completely characterize how a beam of laser light will propagate through water or other fluid. In brief, this technique measures the intensity of light that is scattered through a range of small angles from the original direction of propagation as a result of particles in a detection area. Typically, the pick up angle of the incident (e.g., the scattering angle) varies between 0.1 to about 10 degrees.

Figure 2:
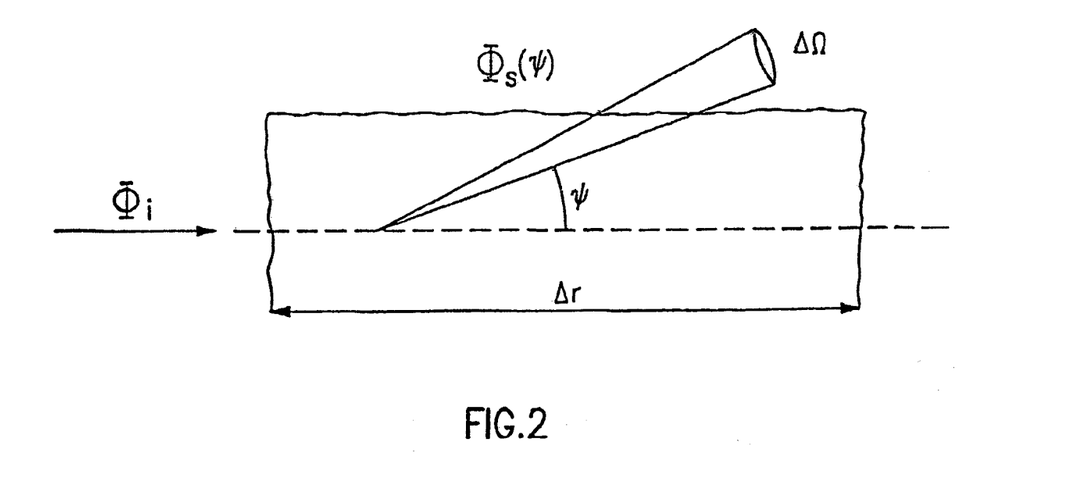
FIG. 2 is a diagrammatical view illustrating the effects of light scattering in a liquid medium from an incident beam.

In theory, the properties of an incident light beam into a liquid medium, such as water, is illustrated in FIG. 2, wherein a narrow, monochromatic collimated beam of light of power $\Phi_i$ becomes incident upon a volume of liquid, having a thickness designated herein as $\Delta r$. Some part of the incident power $\Phi_s$, $(\psi)$ of the beam is scattered into a solid angle $\Delta\Omega$ that is centered upon the scattering angle $\psi$. The resulting function, referred to as the Volume Scattering Function (VSF) is then defined by the following relation:

$$VSF(\psi) = \frac{\Phi_s(\psi)}{\Phi_i \Delta r \Delta\Omega}$$

Figure 3:
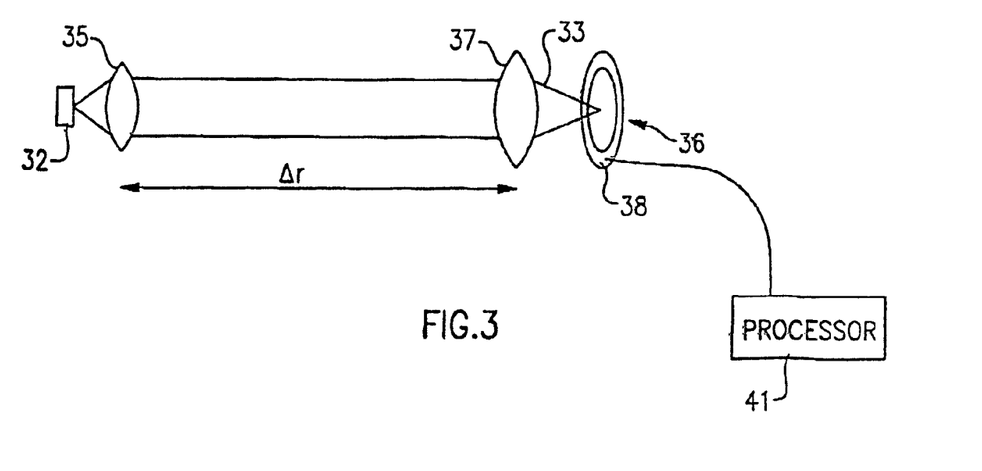
FIG. 3 depicts a diagrammatic view of a low angle light scattering/particle detection system for use in the present invention, the system being depicted to shown unscattered light through a liquid medium.
Figure 4:
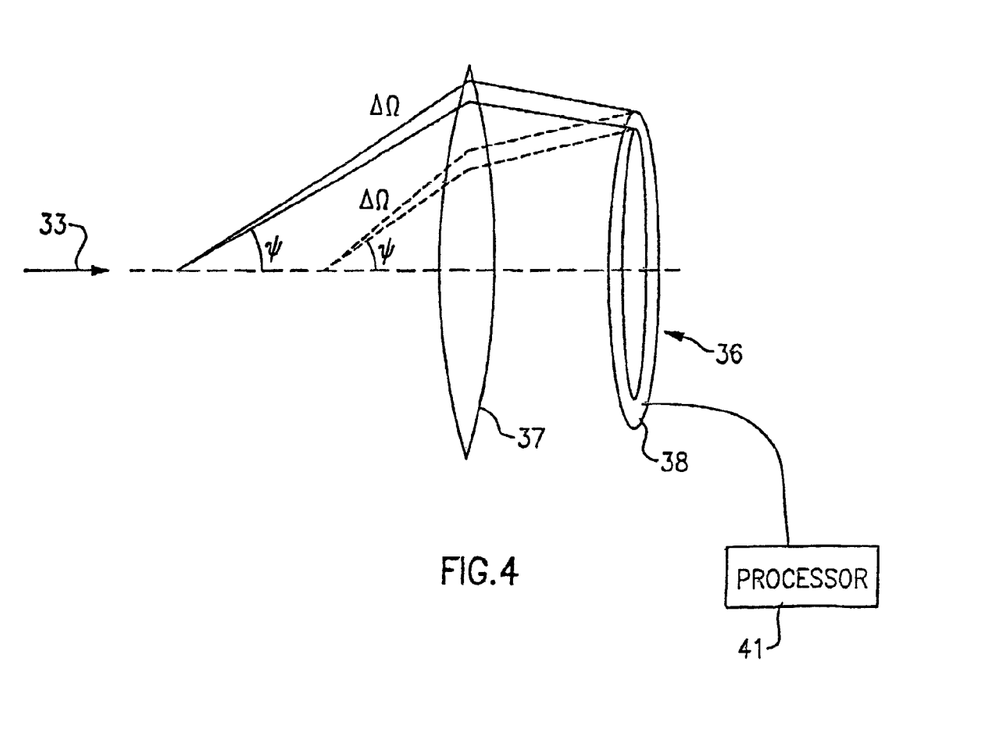
FIG. 4 depicts a partial, diagrammatic view of the low angle light scattering/particle detection system of FIG. 3, as taken during scattering events such as those previously depicted in FIG. 2.

Referring to FIGS. 3 and 4, a low angle scattering/particle measurement system is shown for use in the present invention. A monochromatic light beam 33 is formed by collimating the output of a diode or other form of laser or other type of light emitter 32. Scattered light is detected in this particular instance by means of a detector 36 that is defined by a predetermined number of coaxially arranged rings 38 allowing the passage of unscattered light. FIG. 3 illustrates an unscattered light beam 33 that is initially collimated by means of a lens 33 and is focused onto the center of the detector 36 through a corresponding lens 37. As shown more clearly in FIG. 4, each detector ring 38 is disposed so as to collect the portion of the light beam that is scattered into a particular solid angle $\Delta\Omega$ and defined by a narrow range of scattering angles ($\psi$) relative to the medium, typically on the order of about 0.1 to about 20 degrees. The herein described system is from the LISST Series Particle Measurement Systems, manufactured by Sequoia Scientific, Inc. of Redmond, Wash.

According to the invention, measurement of the Volume Scattering Function (VSF) over the above noted range of pick up angles can therefore be used, by mathematical processing to obtain the size distribution and the concentration of suspended particles in the liquid using a processor 41. The above system can detect particles as small as those having a size in the single micron range and therefore can detect the quantity of agglutinated and nonagglutinated materials in an assay.

Because of its optical nature, the above-described technique is facilitated if the entrance and exit surfaces of a sample container are preferably approximately planar, made from a light transmissive material, and are substantially perpendicular to the angle of incident illumination in order to reduce artifacts that may result from scatter at the container surfaces.

Figure 5:
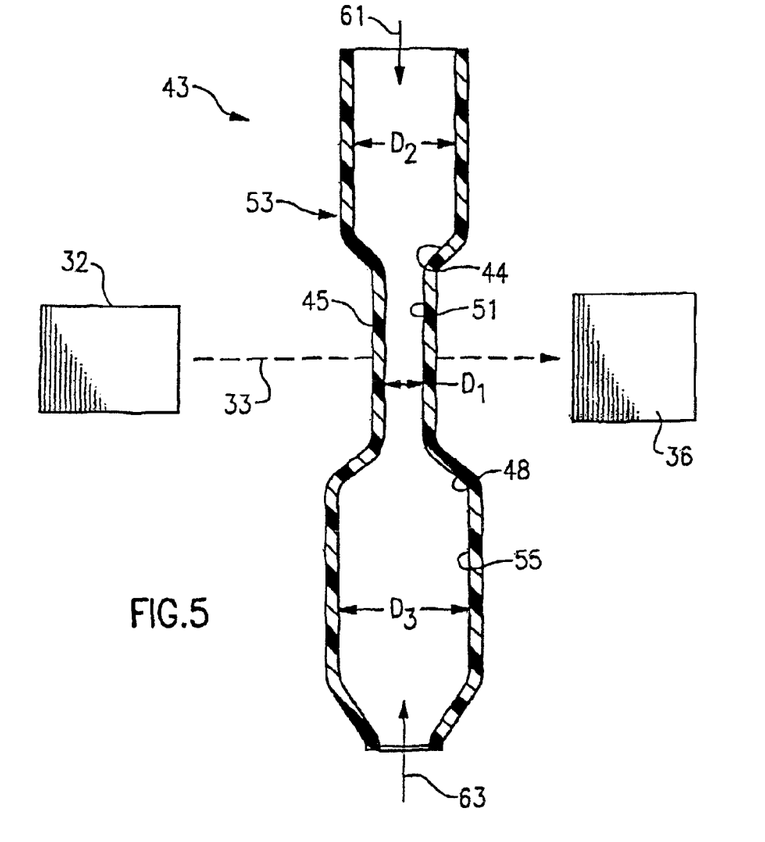
FIG. 5 is a perspective view of a measurement system in accordance with a first embodiment of the present invention.
Figure 6:
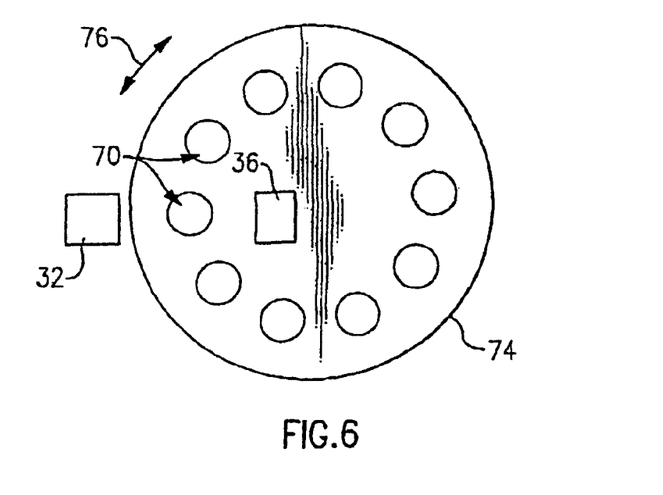
FIG. 6 is a diagrammatic view of a measurement system in accordance with a second embodiment of the present invention.

Referring to FIGS. 5 and 6, two different embodiments are herein described for facilitating agglutination and localizing the particulate materials preferably in conjunction with the low angle scattering/particle detection system of FIGS. 3 and 4. It should be readily discernible, however, that other techniques can be employed within the inventive scope of the present invention.

Referring first to FIG. 5, a low angle light scattering/particle measuring system having a laser emitter 32 and a detector 36, shown only schematically, but as described with regard to FIGS. 3 and 4, is aligned relative to a sample container 43 and more specifically to a measurement window 45 of the container. The lenses 35, 37, FIG. 3, of the measuring system are not shown in this view for reasons of clarity.

The sample container 43 for purposes of this embodiment is defined by three adjacent chamber 51, 53, 55 each linked by a common wall, preferably, each of the chambers being defined by a different inside diameter D1, D2, D3, respectively. As shown, each of $D_2$ and $D_3$ are substantially larger than $D_1$. In order to promote mixing, transition zones 44, 48 are created between adjacent chambers so as to promote an agglutination reaction and more directly so as to create a cloud of cells when agitation of the sample container 43 occurs. A fluid having a predetermined density and viscosity is not required, as in the instance of centrifugation, in order to create mixing. That is to say, mixing can be sufficiently accomplished, for example, through vertical (e.g., up and down) movement of the sample container 43 causing the mixture (not shown) to move, arrows 61, 63 between the adjacent chambers 51, 53, 55 and the transition zones 44, 48 therebetween of the sample container and producing the agglutination reaction as well as the moving field of cells. Depending on the volumes involved, however, the movement could be made at an angle other than vertical. Alternatively, pumps or other aggressive liquid moving means capable of moving a quantity of liquid sample between the adjacent chambers for mixing can be used to draw the fluid between the chambers in a similar manner. For example, a single pump can be used to draw the liquid upwardly into the chambers 51, 53 from chamber 55 wherein the force of gravity will cause the moving flow field to move past the measurement window. The sample container, as well as the various movement mechanism that can be used in conjunction therewith, are described in greater detail in U.S. Pat. No. 7,452,508 and U.S. Patent Publication No. US 2002/0081747, each of which were previously incorporated above by reference in their entirety.

Referring to FIG. 6, a second preferred form of test chamber/testing system relies chiefly upon use of centrifugation as the mechanism for transporting the reaction mixture to the reaction and detection zone. According to one working example, a centrifugation, shown only partially as 74, is used to support a plurality of tubular sample containers 70 into which patient sample is metered. The sample containers are generally as those described with regard to FIG. 1, with some notable exceptions are described in greater detail below. Preferably, each sample container 70 is a tube that includes a planar measurement window such as shown in FIG. 5, to permit detection. Reactant material (e.g., red blood cells) is preferably contained in an upper portion of the container and a receiving fluid having a specified density and viscosity is provided in a lower portion (not shown) of the container. This material can include at least one liquid having a higher specific gravity than that of the blood cells. The other properties herein contained of this at least one additional fluid are designed to produce an environment that maintains the integrity of the red blood cells.

As noted and though the present method specifically describes agglutination reactions with regard to blood typing, it should be apparent to one of sufficient skill and as described in greater detail below that there is potential to use antigen carriers other than red blood cells in that the herein described particle detection system does not depend on the red color of the cells.

First and with regard to centrifugation, reference is now made to FIGS. 7-10, herein describing a proposed testing procedure for A-B-O blood typing (FIGS. 9, 10), each using the presently described method.

Figure 7:
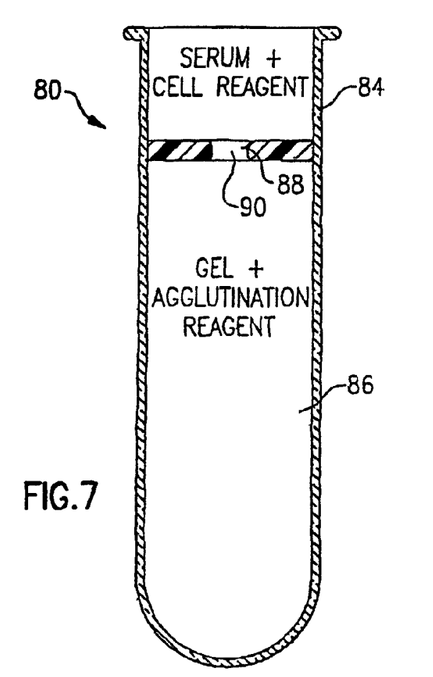
FIG. 7 is a side elevational view, taken in section of a sample container made in accordance with a preferred embodiment of the present invention.

As noted, the sample containers 80 used in each of the above tests are somewhat similar to those described with regard to FIG. 1. However, the restriction orifice 88 located between the upper portion 84 of the container and the lower portion 86 thereof is optional since spatial separation is not the preferred mode by which the cells are classified following reaction. Preferably, however, a restriction orifice is added that promotes a dispersion of cells into a moving flow field. This restriction orifice, however, is sized to be smaller than those of previously known systems requiring both chemical separation and spatial separation. The restriction orifice for this embodiment for example is approximately 1 millimeter as opposed to a 4 millimeter diameter required in known containers.

A receiving fluid containing an agglutination reagent is added to the lower portion of the sample container, either as filled within a clinical analyzer (not shown) or sold as a prefilled quantity, the agglutination reagent being mixed with the receiving fluid to form a homogenous mixture.

In the upper portion 84 of the sample container 80, a patient serum is first added, followed by a RBC (red blood cell) or other suitable reagent, the serum and reagent being added preferably by means of a metering mechanism or pipette tip (not shown). The edges of the restriction orifice 88 provide a latch point for the metered serum material, thereby forming an air bubble 90 between the gel/reagent mixture and the serum/RBC reagent prior to the application of the centrifugal force.

As to the constitution of the receiving fluid, a sugar-based or other material having a density chosen to permit the red blood cells to move through it at a specified rate under centrifugal force is preferred.

Figure 7A:
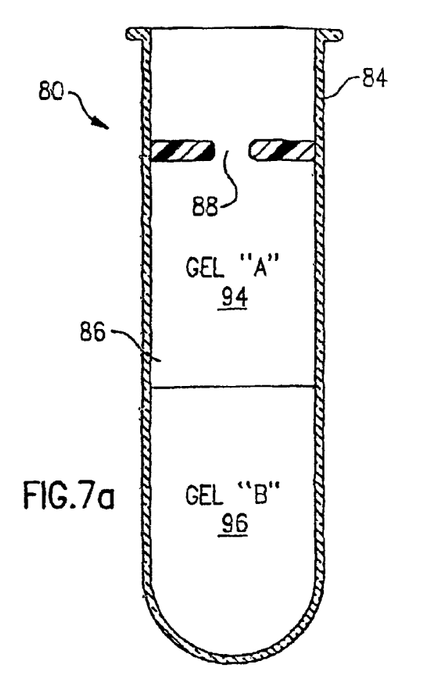
FIG. 7(a) is a side elevational view, also taken in section, of a sample container according to an alternative embodiment of the invention.

According to an alternate embodiment, as shown in FIG. 7(a), the sample container 80 can include two or more materials, designated 94 and 96, respectively having differing material (density) properties. Preferably, a higher density material can be provided in the lowest portion of the container while a lower density material can be provided in an intermediate portion of the container. According to this alternate embodiment, the red blood cells would cease migrating when they reach a neutral buoyancy rate. The latter is less sensitive to centrifugation, force and time and therefore may enable more rapid centrifugation of the sample container.

Figure 8:
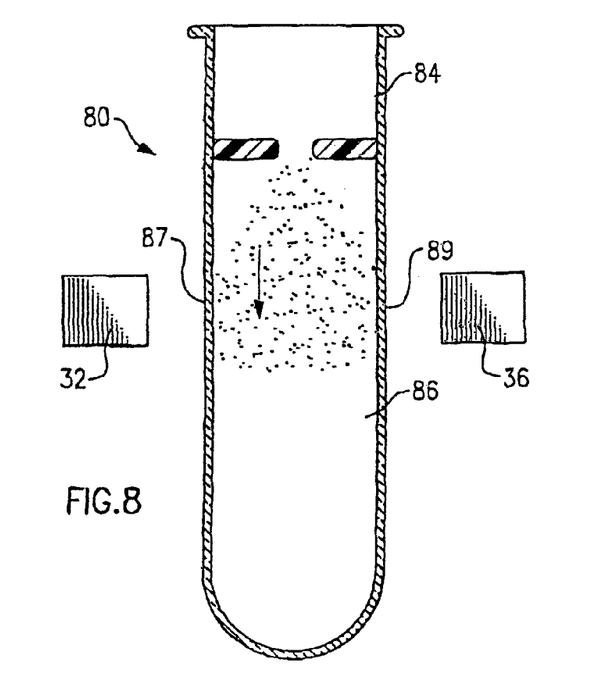
FIG. 8 is the side elevational view of the sample container of FIG. 7, depicting the movement of a flow field in relation to the measurement system of FIG. 3.

Still referring to FIGS. 7 and 8, the sample container 80 is incubated wherein the bound antibody is bound to the red blood cells. The sample container 80 is then centrifuged and test spun in order to group the cells and force same through the restriction orifice 88 where the cells are dispensed into a moving flow field into the reagent matrix below. The centrifuge promotes the agglutination reaction vis a vis the contained reagent. The moving cell field is pushed as a "cloud" into the measurement windows 87, 89 of the container 80 wherein the particle detection system 32, 36 determines the size distribution of particles in order to determine the strength of agglutination.

The above read process can occur in several ways: First, the read can occur during centrifugation if synchronized with the rotation of the centrifuge. This read technique provides real time data relating to the state of the cells moving through the media, thereby making the measurement insensitive to the final position and minimizing the time to result, especially for strong agglutination reactions.

Alternately, the read process can also occur after the completion of centrifugation, but can proceed while the container (e.g. tube) is still within the centrifuge. This enables consolidation of hardware and uses the centrifuge as the location device that holds the tube(s) in fixed position. In the embodiment shown, the light emitter 32 and detector 36 of the light scattering/particle detection system are arranged in a fixed location relative to the centrifuge, as the centrifuge rotates the tubes therebetween, per arrow 76. Each of the above read process steps can therefore be accomplished using this type of system station positioning.

Alternatively, the above read/detection process can also be performed as a separate or off line procedure in which the tubes 70 can be placed in a separate device/apparatus (not shown) following the centrifugation process. This latter process may be required if there are space/size or other unique requirements that are not available internally to the centrifuge.

Therefore, the sample container can be removed or remain in the centrifuge for either an end point measurement or alternately an "on the fly" measurement can be made in which at least one image can be obtained while the centrifuge is slowing down or through use of a strobe.

Alternative centrifugation techniques, for example, involving a fixed angled centrifuge can be similarly utilized. This technique has been shown to create a "smear" of cells along the wall of the tubular sample container. A high-resolution vision system or a low-angle particle analysis system such as that shown in FIGS. 3 and 4 can then inspect these cells. As with a swinging bucket centrifuge, it is possible to read the test tubes in the centrifuge, during or after centrifugation, or after the tubes have been removed from the centrifugation in a separate apparatus.

Figure 9:
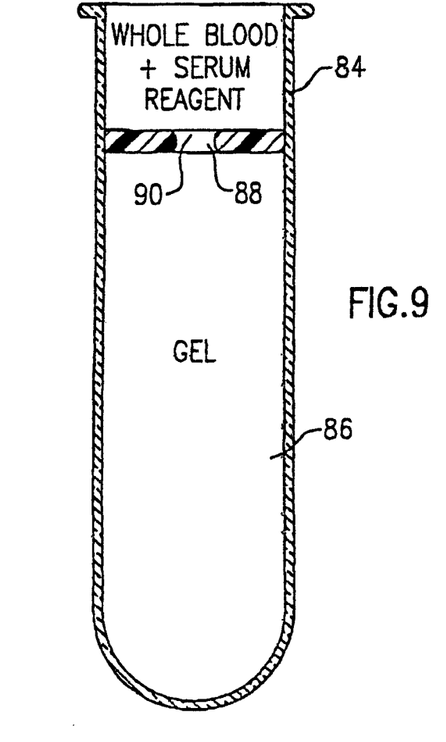
FIG. 9 is a side elevational view of a sample container made in accordance with the present invention.
Figure 10:
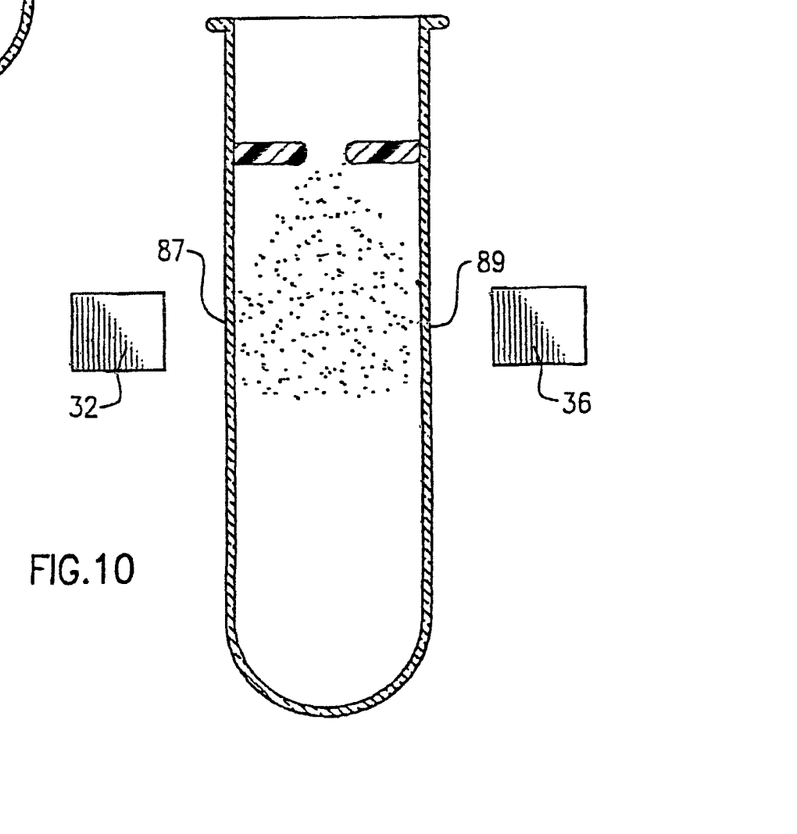
FIG. 10 is a side elevational view of the sample container of FIG. 9.

Referring to FIGS. 9 and 10, a similar sample container 80 is shown for A-B-O blood typing preferably having a smaller restriction orifice, as compared to those of the prior art, for example FIG. 1, in order to promote disposition of a moving flow field. According to the technique, whole blood and a liquid serum reagent are each added to the upper portion 84 of a sample container 80. A gel is added to the bottom portion 86 of the sample container 80, the gel having a density and viscosity that is lower than that of the agglutinated red blood cells to promote movement therethrough as a flow field.

The sample container 80 is incubated sufficiently and centrifugation forces intimation of the cells, enhancing the agglutination reaction as the cells are dispensed through the restriction orifice 88 into the gel matrix and past the measurement windows 87, 89 permitting scanning by the detection system 32, 36.

Using a test chamber set-up as shown in FIG. 5, an A-B-O blood typing procedure/testing is performed by aspirating whole blood and serum reagent into the confines of the container and then promoting movement between the transition zones of the tip, thereby creating the agglutination reaction. An air bubble interface between the compartments of the container is optional for this type of testing.

As previously noted, other forms of classification detection can be performed using the above-described methodology.

Antibody detection can also be performed using a sample container 100 similar in design to that depicted according to FIG. 5. According to this technique, serum cell material is initially aspirated into the container 100. RBC reagent is then additionally aspirated into the container 100. The serum and the RBC reagent are then mixed through means of vertical agitation using a pump or other means in order to create bound antibodies. The sample container 100 is then axially spun by centrifuge or other means, the container preferably having a compartment (not shown) within the same into which the cells are trapped as described in U.S. Pat. No. 4,933,291 to Daiss et al., the entire contents of which are incorporated by reference.

Surplus material (reagent, serum, unbound antibodies) is then discharged from the sample container 100 and a wash fluid is aspirated into the container to wash the cells wherein the wash fluid and cells are suspended and the sample container is axially spun. The wash fluid is then discarded and agglutination reagent is then aspirated into the sample container. The cell/reagent mixture is resuspended and mixed by vertical agitation to create an agglutination reaction by means of the transition zones after which the passing mixture is read using the particle detection system and determining a size distribution of the passing particles.

Figure 11:
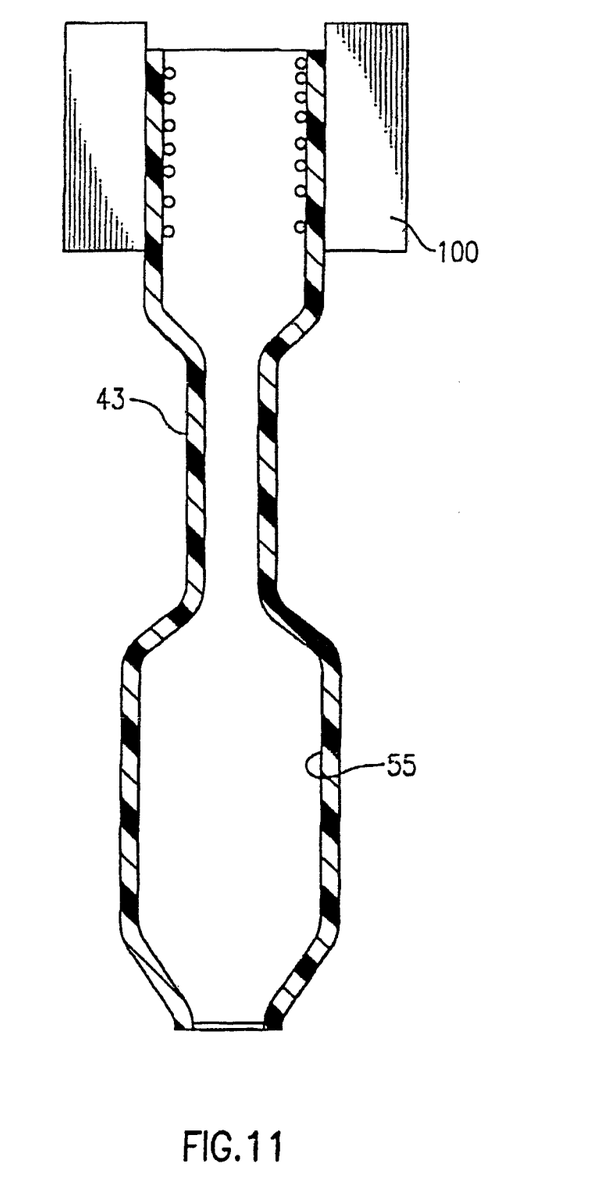
FIG. 11 is a flow chart illustrating a method for performing antibody detection in accordance with another preferred embodiment of the invention using the measurement system of FIG. 5.

Referring to FIG. 11, and in lieu of using a separate compartment, and axial spin (e.g., centrifugation) a magnetic bead or particle can be alternately attached to each cell/bound antibody. The sample container 43 can then be placed within a toroidal magnet 100, suspending the cells, permitting discharge of surplus material and use of a wash fluid to first wash unbound antibody from the cells and then adding an agglutination reagent, the magnet being used to retain the bound cells in the container 43 between washes and other processing steps.

PARTS LIST FOR FIGS. 1-11

10 cartridge
12 sample container
14 sample container
16 sample container
18 tubular sample container
19 band, agglutination
20 sample container
21 reaction zone, initial
22 sample container
23 upper portion
25 lower portion
26 button of cells
30 matrix of inert particles
32 light emitter
33 light beam
35 lens
36 light detector
37 lens
38 detector rings
41 processor
43 sample container
44 transition zone
48 transition zone
51 chamber
53 chamber
55 chamber
61 arrow
63 arrow
70 sample container
74 centrifuge
76 arrow
80 sample container
84 upper portion
86 lower portion
87 measurement window
98 restriction orifice
89 measurement window
90 air bubble
92 gel material
94 gel material
100 magnet
$\Phi_i$ beam power, incident
VFS volume scattering function
$\Delta r$ thickness, scattering volume
$\Delta \Omega$ solid scattering angle
$\psi$ scattering or pick up angle
$\Phi_s$ scattered power of part of incident beam Though the invention has been described in terms of certain embodiments, it will be readily apparent that there variations and modifications that can be performed that still embody the inventive scope of the invention, as defined by the following claims.

The invention claimed is:

1. A method of classifying a patient sample, said method comprising the steps of:

providing a patient sample and at least one agglutination reagent into the confines of a sample container, said patient sample being disposed in an upper portion of said sample container and said at least one agglutination reagent being disposed in a lower portion of said sample container, said upper and lower portions separated by a restriction orifice;

moving the patient sample and at least one reagent within the sample container under centrifugation such said sample and said at least one reagent are sufficiently mixed so as to produce an agglutination reaction, including the step of providing at least one receiving fluid in said container having a specific viscosity and specific gravity to effectively exclude the sample prior to centrifugation thereof, but which allows particles within said sample to move therethrough when centrifugal force is applied while excluding small molecules and controlling the rate at which the material is moved within the fluid wherein only cells are subsequently moved as a flow field through the restriction orifice of said container and past an intermediately disposed measurement window of the sample container;

scanning a monochromatic light beam into the measurement window of the sample container and probing the moving flow field with the light beam of a low angle particle measurement system in which agglutinated cells of said sample in said moving flow field scatter light based on the presence of said cells and the sizing thereof; and detecting at a light detector of the measurement system, the size and amount of said cells (both free cells and agglutinated cells) of said moving flow field based on the detection of scattered light based on the volume scattering function (VSF) of said light which is caused by the presence of said agglutinated cells in said moving flow field, said detector including a predetermined number of coaxially arranged detector rings which are arranged opposite said light beam in relation to said measurement window, each said detector ring being disposed to receive light scattered at a predetermined scattering angle, said coaxially arranged detector rings being defined to receive light scattered over a range of about 0.1 to about 20 degrees, wherein unscattered light is focused by at least one lens onto the center of said detector and in which said probing and detecting steps are performed prior to endpoint of said reaction.

2. A method as recited in claim 1, wherein said patient sample is a blood sample.

3. A method as recited in claim 1, wherein said sample container includes at least one chamber having a smaller inside diameter than an adjacent chamber of said container through which the mixture is moved.

4. A method as recited in claim 1, including the step of determining the size distribution of agglutinated cells in said moving flow field.

5. A method as recited in claim 1, wherein said detection step includes the step of blood typing based on the detected characteristics of said agglutinated cells.

* * * * *